US009113837B2

United States Patent
Li et al.

(10) Patent No.: US 9,113,837 B2
(45) Date of Patent: Aug. 25, 2015

(54) DROWSINESS DETECTION METHOD AND ASSOCIATED DEVICE

(71) Applicant: Wistron Corporation, New Taipei (TW)

(72) Inventors: Chia-Hsien Li, New Taipei (TW); Yao-Tsung Chang, New Taipei (TW); Pai-Yang Lin, New Taipei (TW)

(73) Assignee: WISTRON CORPORATION, New Taipei (TW)

( * ) Notice: Subject to any disclaimer, the term of this patent is extended or adjusted under 35 U.S.C. 154(b) by 159 days.

(21) Appl. No.: 13/662,968

(22) Filed: Oct. 29, 2012

(65) Prior Publication Data
US 2013/0176129 A1   Jul. 11, 2013

(30) Foreign Application Priority Data

Jan. 6, 2012   (TW) .............................. 101100663 A

(51) Int. Cl.
*G08B 23/00* (2006.01)
*A61B 5/18* (2006.01)
(Continued)

(52) U.S. Cl.
CPC .............. *A61B 5/18* (2013.01); *B60R 21/01552* (2014.10); *G06K 9/00845* (2013.01);
(Continued)

(58) Field of Classification Search
CPC .......... G08B 21/06; G08B 23/00; A61B 5/18; A61B 2503/22; A61B 5/0484; A61B 5/1103; A61B 5/7264; B60R 21/01552; G06K 9/00845
USPC ....................................................... 340/575
See application file for complete search history.

(56) References Cited

U.S. PATENT DOCUMENTS 4,408,616 A * 10/1983 Duffy et al. ................... 600/544
5,259,390 A * 11/1993 MacLean ...................... 600/552
(Continued)

FOREIGN PATENT DOCUMENTS

CN   101969849 A   2/2011
CN   102046086 A   5/2011
(Continued)

OTHER PUBLICATIONS

CN Office Action dated May 5, 2014.
(Continued)

*Primary Examiner* — Quang D Pham
(74) *Attorney, Agent, or Firm* — McClure, Qualey & Rodack, LLP

(57) ABSTRACT

A drowsiness detection method for detecting drowsiness of a detection target is provided. The method includes a data collecting process including steps of: detecting physiological symptom information of the detection target; determining whether the detection target satisfies a predetermined drowsiness threshold condition according to the physiological symptom information; when the detection target satisfies the predetermined drowsiness threshold condition, triggering a stimulation event on the detection target; determining whether a response event is received from the detection target in response to the stimulation event; when the response event is not received, determining whether the stimulation event satisfies a threshold strength condition; and recording the physiological symptom information as a corresponding drowsiness detection condition of the detection target when the stimulation event satisfies the threshold strength condition.

12 Claims, 4 Drawing Sheets

(51) Int. Cl.
  B60R 21/015 (2006.01)
  G06K 9/00 (2006.01)
  G08B 21/06 (2006.01)
  *A61B 5/00* (2006.01)
  *A61B 5/0484* (2006.01)
  *A61B 5/11* (2006.01)

(52) U.S. Cl.
  CPC ............... G08B21/06 (2013.01); G08B 23/00 (2013.01); *A61B 5/0484* (2013.01); *A61B 5/1103* (2013.01); *A61B 5/7264* (2013.01); *A61B 2503/22* (2013.01)

(56) References Cited

U.S. PATENT DOCUMENTS

| | | | | |
|---|---|---|---|---|
| 5,311,877 | A * | 5/1994 | Kishi | 600/545 |
| 6,070,098 | A * | 5/2000 | Moore-Ede et al. | 600/544 |
| 6,353,396 | B1 * | 3/2002 | Atlas | 340/693.9 |
| 6,805,668 | B1 * | 10/2004 | Cadwell | 600/300 |
| 7,225,013 | B2 * | 5/2007 | Geva et al. | 600/513 |
| 7,970,459 | B2 * | 6/2011 | Karasudani | 600/509 |
| 7,982,620 | B2 * | 7/2011 | Prokhorov et al. | 340/576 |
| 8,033,998 | B2 * | 10/2011 | Bullens et al. | 600/484 |
| 8,131,352 | B2 * | 3/2012 | Greene | 600/544 |
| 8,140,149 | B2 | 3/2012 | Hatakeyama et al. | |
| 8,298,153 | B2 * | 10/2012 | Boute et al. | 600/508 |
| 8,606,356 | B2 * | 12/2013 | Lee et al. | 607/17 |
| 8,666,603 | B2 * | 3/2014 | Morris | 701/42 |
| 8,766,819 | B2 * | 7/2014 | Dorfmann et al. | 340/945 |
| 8,855,775 | B2 * | 10/2014 | Leyde | 607/45 |
| 2004/0243013 | A1 * | 12/2004 | Kawachi et al. | 600/509 |
| 2008/0319335 | A1 * | 12/2008 | Greene | 600/544 |
| 2009/0171232 | A1 * | 7/2009 | Hu et al. | 600/545 |
| 2009/0275847 | A1 * | 11/2009 | Karasudani | 600/509 |
| 2010/0033333 | A1 * | 2/2010 | Victor et al. | 340/576 |
| 2010/0049066 | A1 * | 2/2010 | Hatakeyama | 600/509 |
| 2011/0021866 | A1 * | 1/2011 | Iizuka et al. | 600/26 |
| 2011/0230783 | A1 * | 9/2011 | Bartol et al. | 600/546 |
| 2011/0288424 | A1 * | 11/2011 | Kanai et al. | 600/500 |
| 2011/0319721 | A1 * | 12/2011 | Hamaguchi | 600/300 |
| 2012/0029302 | A1 * | 2/2012 | Hsu et al. | 600/300 |
| 2012/0212353 | A1 * | 8/2012 | Fung et al. | 340/905 |
| 2012/0221171 | A1 * | 8/2012 | Shirakata et al. | 701/1 |
| 2013/0072810 | A1 * | 3/2013 | Wingeier et al. | 600/544 |
| 2013/0207804 | A1 * | 8/2013 | Li et al. | 340/575 |
| 2014/0062704 | A1 * | 3/2014 | Kubotani et al. | 340/575 |
| 2014/0107506 | A1 * | 4/2014 | Lee et al. | 600/508 |

FOREIGN PATENT DOCUMENTS

| | | |
|---|---|---|
| TW | 200929089 A | 7/2009 |
| TW | M364383 | 9/2009 |

OTHER PUBLICATIONS

Partial English translation of CN Office Action dated May 5, 2014.
TW Office Action dated Jul. 7, 2014.
Partial English translation of TW Office Action dated Jul. 7, 2014.
Partial English translation of TWM364383 (Publisehd Sep. 1, 2009).

* cited by examiner

DROWSINESS DETECTION METHOD AND ASSOCIATED DEVICE

This application claims the benefit of Taiwan application Serial No. 101100663, filed Jan. 6, 2012, the subject matter of which is incorporated herein by reference.

BACKGROUND OF THE INVENTION

1. Field of the Invention

The invention relates in general to a drowsiness detection device and associated method, and more particularly, to a drowsiness detection device and associated method for determining a drowsiness detection condition through a stimulation event triggered on a detection target and a corresponding response from the detection target.

2. Description of the Related Art

As the technology continuously progresses in the modern world, drowsiness detection devices are developed to provide a user a solution for detecting drowsiness in circumstances where the user needs to stay awake. A current drowsiness detection device generally detects various physiological signals of a detection target user, and compares detected physiological signals with existing threshold conditions to perform drowsiness detection on the detection target user.

With respect of detection target users of different ages, genders and ethnic groups, conditions of drowsiness may be represented in quite different physiological symptoms, making an accurate drowsiness detection operation on the diversified detection target users an extremely challenging task for a conventional drowsiness detection device. Therefore, there is a need for a solution for providing an accurate drowsiness detection operation adaptively suitable for all kinds of detection target users.

SUMMARY OF THE INVENTION

According to an aspect of the present invention, a drowsiness detection method is provided for performing a drowsiness detection operation on a detection target. The method includes a data collecting process includes steps of: detecting a first physiological symptom information of the detection target; determining whether the detection target satisfies a predetermined drowsiness threshold condition according to the first physiological symptom information; when the detection target satisfies the predetermined drowsiness threshold condition, triggering a stimulation event on the detection target; determining whether a response event is received from the detection target in response to the stimulation event; when the response event is not received, determining whether the stimulation event satisfies a threshold strength condition; and recording the physiological symptom information as a corresponding drowsiness detection condition of the detection target when the stimulation event satisfies the threshold strength condition.

According to another aspect of the present invention, a drowsiness detection device is provided for performing a drowsiness detection operation on a detection target. The device includes a detection/control circuit, a stimulation triggering circuit and a response circuit. The detection/control circuit detects a first physiological symptom information of the detection target, accordingly determines whether the detection target satisfies a predetermined drowsiness threshold condition, and provides a driving signal when the detection target satisfies the predetermined drowsiness threshold condition. The simulation triggering circuit triggers a stimulation event on the detection target in response to the driving signal. The response circuit detects a response event triggered by the detection target in response to the stimulation event, and accordingly provides a response signal. The detection/control circuit further determines whether the detection target triggers the response event according to the response signal. When the detection target does not trigger the response event, the detection/control circuit further determines whether the simulation event satisfies a threshold strength condition. When the stimulation event satisfies the threshold strength condition, the detection/control circuit records the first physiological symptom information as a drowsiness detection condition corresponding to the detection target.

The above and other aspects of the invention will become better understood with regard to the following detailed description of the preferred but non-limiting embodiments. The following description is made with reference to the accompanying drawings.

DETAILED DESCRIPTION OF THE INVENTION

Figure 1:
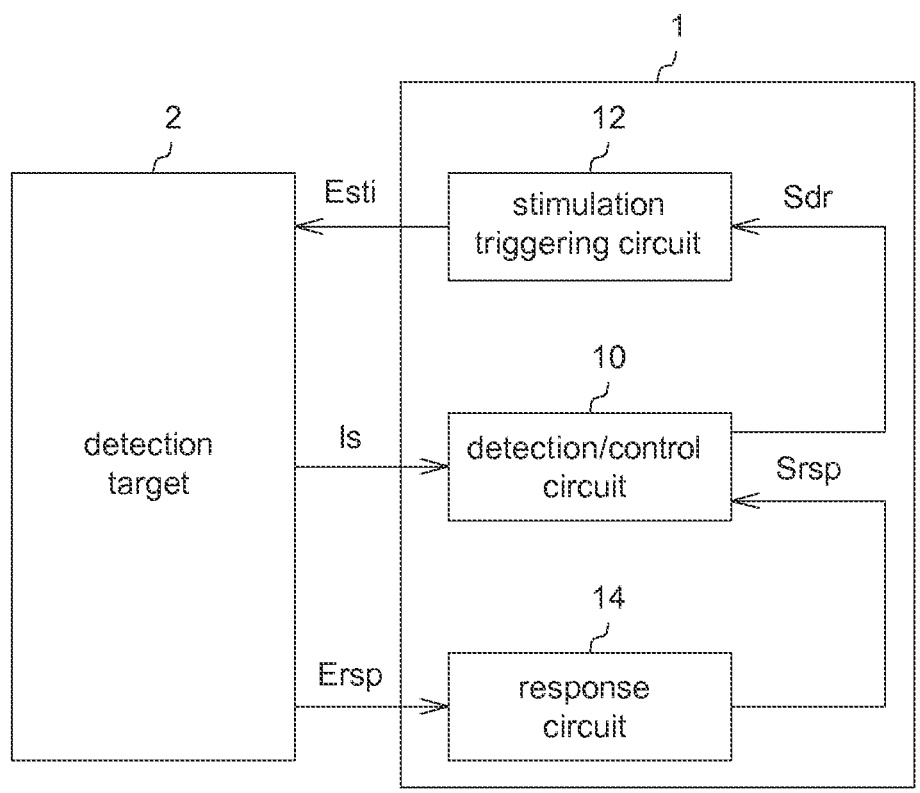
FIG. 1 is a block diagram of a drowsiness detection device according to an embodiment of the present invention.

FIG. 1 shows a block diagram of a drowsiness detection device according to an embodiment of the present invention. A drowsiness detection device 1 performs a drowsiness detection operation on a detection target 2, e.g., a user under detection. The drowsiness detection device 1 includes a detection/control circuit 10, a stimulation triggering circuit 12 and a response circuit 14. Under the control of the detection/control circuit 10, the stimulation triggering circuit 12 provides a driving signal Sdr for triggering a stimulation event Esti on the detection target 2. For example, the stimulation triggering circuit 12 may be any user interface output device such as a speaker, a vibrator or a lighting equipment, which provides the stimulation event Esti in form of a sound, a vibration or a glittering beam in response to the driving signal Sdr.

The response circuit 14 detects whether the detection target 2 triggers a corresponding response event Ersp in response to the stimulation event Esti to accordingly provide a response signal Srsp. For example, the response circuit 14 may be any user interface input device such as a keyboard, a mouse, a touch pad, a button, a switch, an audio identification device, a visual identification device or an infrared sensor, which determines whether the detection target 2 triggers a corresponding man-machine-interface response event to accordingly provide the response signal Srsp.

Figure 2:
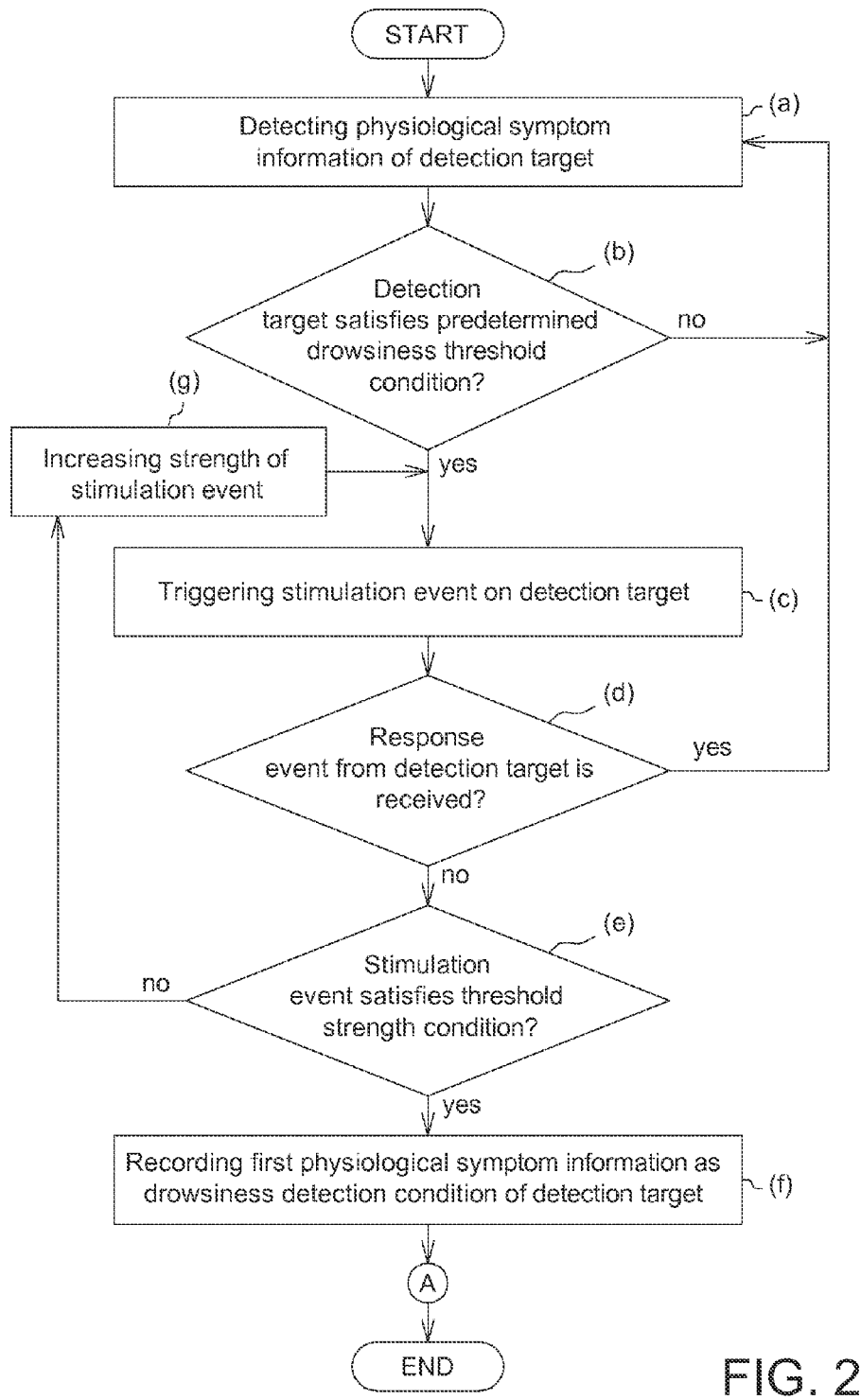
FIG. 2 is a flowchart of a data collecting process in a drowsiness detection method according to an embodiment of the present invention.

The detection/control circuit 10, coupled to the stimulation triggering circuit 12 and the response circuit 14, performs the drowsiness detection method and controls the drowsiness detection device 1 to perform the drowsiness detection operation on the detection target 2. FIG. 2 shows a flowchart of a data collecting process in the drowsiness detection method according to an embodiment of the present invention. For example, the drowsiness detection method of the embodiment includes a data collecting process including the following steps. In Step (a), the detection/control circuit 10 detects physiological symptom information Is of the detection target 2. For example, the detection/control circuit 10 selectively includes a brainwave detecting unit, an image capturing unit, a heartbeat detecting unit, a breath detecting unit, and/or a driving status detecting unit to obtain brainwave information, eye blinking frequency information, head swinging information, heartbeat information, breathing frequency information and driving status information to accordingly obtain the physiological symptom information Is.

For example, the predetermined drowsiness threshold condition is a drowsiness threshold standard determined by the foregoing information of various physiological symptoms. Assume that the physiological symptom information Is includes the eye blinking frequency information, and the drowsiness threshold condition is correspondingly a frequency threshold. When the eye blinking frequency corresponding to the eye blinking frequency information is substantially smaller than the frequency threshold, the detection/control circuit 10 determines that the detection target 2 is not in a predetermined drowsy state and does not satisfy the predetermined drowsiness threshold condition. Based on the similar principle, assuming that the physiological symptom information Is includes other signals, the detection/control circuit 10 determines whether the detection target 2 satisfies the predetermined drowsiness threshold according to the corresponding threshold to further determine whether the detection target 2 is in a predetermined drowsy state.

In Step (b), the detection/control circuit 10 determines whether detection target 2 satisfies the predetermine drowsiness threshold condition according to the physiological symptom information Is. When the detection target 2 does not satisfy the predetermine drowsiness threshold condition, the process iterates Step (a) to repeatedly detect the physiological symptom information Is of the detection target 2. When the detected physiological symptom information Is of the detection target 2 satisfies the predetermined drowsiness threshold condition, the drowsiness detection method of the embodiment performs Step (c). In Step (c), the detection/control circuit 10 provides a driving signal Sdr to drive the stimulation triggering circuit 12 to trigger the stimulation event Esti on the detection target 2.

Within a predetermined period after Step (c), the drowsiness detection method of the embodiment performs Step (d). In Step (d), the detection/control circuit 10 determines whether the response event Ersp triggered by the detection target 2 in response to the stimulation event Esti is received via the response circuit 14. When the response event Ersp is received, it means that the detection target 2 spontaneously responds to the stimulation event Esti within a predetermined period, and so it is inferred that a mental state of the detection target 2 is not in a drowsy state. Accordingly, the drowsiness detection method returns to Step (a) to continue in detecting the physiological symptom information Is of the detection target 2.

Conversely, when the detection/control circuit 10 does not detect/receive the response event Ersp within the predetermined period, it means the detection target 2 does not spontaneously respond to the stimulation event Esti, and so it is inferred that the detection target 2 is much likely in a drowsy state. Accordingly, the drowsiness detection method of the present invention performs Step (e) after Step (d). In Step (e), the detection/control circuit 10 further determines whether the stimulation event Esti satisfies a threshold strength condition. For example, the threshold strength condition is associated with the strength of the sensory stimulation of the stimulation event Esti triggered on the detection target 2. Assuming that the stimulation triggering circuit 12 is a speaker, for example, the threshold strength condition is a volume threshold for indicating the stimulation event Esti (e.g., the speaker generating a sound). When the volume of sound sent from the speaker is substantially smaller than the volume threshold, the detection/control circuit 10 correspondingly determines that the stimulation event Esti does not satisfy the threshold strength condition. Conversely, when the volume of the sound sent from the speaker is substantially greater than the volume threshold, the detection/control circuit 10 correspondingly determines that the stimulation event Esti satisfies the threshold strength condition.

When the stimulation event Esti satisfies the threshold strength condition, it means the strength of the stimulation event Esti triggered on the detection target 2 by the drowsiness detection device 1 is quite high, and yet the detection target 2 does not spontaneously respond to the stimulation event Esti. That is to say, the detection target 2 is much likely in a drowsy state. Accordingly, the drowsiness detection method of the embodiment performs Step (f). In Step (f), the detection/control circuit 10 records the physiological symptom information Is as the drowsiness detection condition corresponding to the detection target 2.

Conversely, when the stimulation event Esti does not satisfy the threshold strength condition, it means the strength of the simulation event Esti triggered on the detection target 2 by the drowsiness detection device 1 does not correspond to an upper limit. Accordingly, the drowsiness detection method of the embodiment performs Step (g). In Step (g), the detection/control circuit 10 increases the strength of the stimulation event Esti, and iterates Step (c) to provide the detection target 2 with the stimulation event Esti having the increased strength.

In conclusion, in the data collecting process, the drowsiness detection device 1 of the embodiment tests the detection target 2 with stimulations and response detections performed by the stimulation triggering circuit 12 and the response circuit 14, and truly records the corresponding physiological symptom information Is as the detection target 2 enters a drowsy state.

In this embodiment, an example of the drowsiness detection method including the data collecting process is taken for illustrative purposes rather than limiting the present invention thereto. In an alternative example, the drowsiness detection method of the embodiment may also repeatedly iterate the data collecting process to correspondingly record a multiple drowsiness detection conditions. After obtaining multiple drowsiness detection conditions, the drowsiness detection method further performs a detection condition training process to identify an adaptive mental state determining condition according to the drowsiness detection conditions. For example, the detection condition training process is performed by the detection/control circuit 10. In yet another example, the detection/control circuit 10 further provides the multiple drowsiness detection conditions to a rear-end server, which then correspondingly executes related operational processes.

Figure 3:
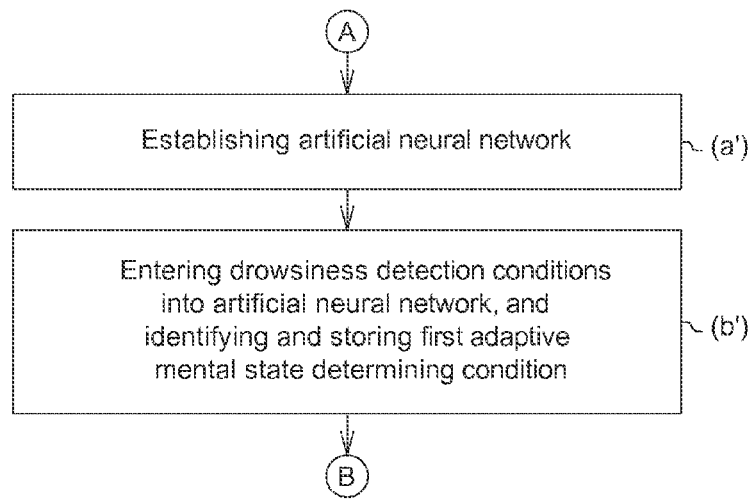
FIG. 3 is a flowchart of a detection condition training process in a drowsiness detection method according to an embodiment of the present invention.

FIG. 3 shows a detection condition training process in a drowsiness detection method according to an embodiment of the present invention. In the descriptions below, an example of a rear-end server executing the detection condition training process shall be given to further explain the detection condition training process in a drowsiness detection method according to an embodiment of the present invention. For example, the detection condition training process of the embodiment includes the following steps. In Step (a'), the rear-end server establishes an artificial neural network N. In Step (b'), the rear-end server enters the multiple drowsiness detection conditions into the artificial neural network N, and identifies an adaptive mental state determining condition Ca via related data analysis, parameter prediction and characteristic value calculations.

Assume that the physiological symptom information Is corresponding to the multiple drowsiness detection conditions is brainwave information. Each of the drowsiness detection conditions records one brainwave time-domain waveform of the detection target 2 at a time point as the detection target enters a drowsy state. The brainwave time-domain waveform may be converted to be denoted in four basic component wavebands of α (e.g., corresponding to a frequency band of 8 to 14 Hz), β (e.g., corresponding to a frequency band of above 14 Hz), θ (e.g., corresponding to a frequency band of 4 to 8 Hz), and δ (e.g., corresponding to a frequency band of 0.04 to 4 Hz). In other words, the drowsiness detection conditions correspond to multiple brainwave time-domain waveforms of the detection target 2 as the detection target 2 enters a drowsy state. In Step (b'), the rear-end server provides the components α, β, θ and δ as input information to the artificial neural network N, and identifies the adaptive mental state determining condition Ca through a corresponding artificial neural network training method. For example, the adaptive mental state determining condition Ca represents a strength distribution standard of the components α, β, θ and δ of the brainwave time-domain waveform at a time point as the detection target 2 enters a drowsy state.

Figure 4:
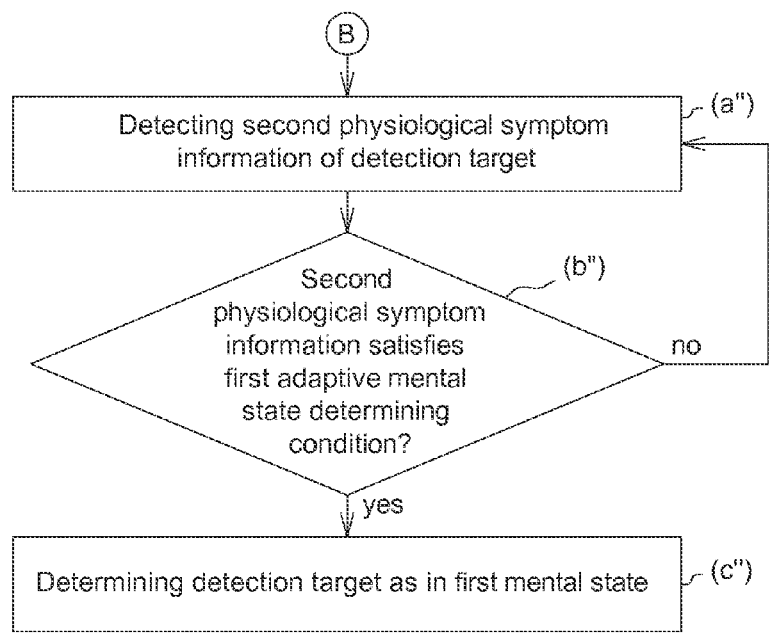
FIG. 4 is a flowchart of a drowsiness monitoring process in a drowsiness detection method according to an embodiment of the present invention.
Figure 5:
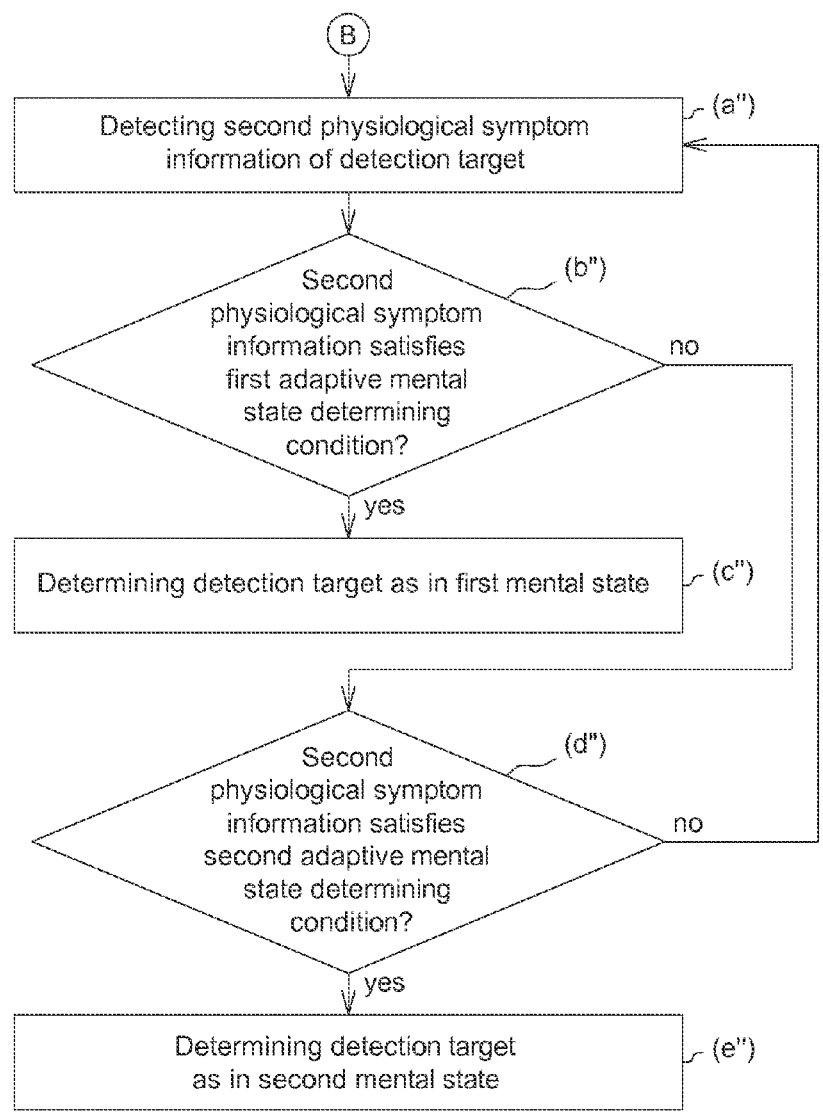
FIG. 5 is a flowchart of a drowsiness monitoring process in a drowsiness detection method according to another embodiment of the present invention.

FIG. 4 shows a flowchart of a drowsiness monitoring process in a drowsiness detection method according to an embodiment of the present invention. After the detection condition training process, the rear-end server further loads the adaptive mental state determining condition Ca into the detection/control circuit 10. The detection/control circuit 10 then performs the drowsiness monitoring process in the drowsiness detection method of the embodiment to determine a mental state of the detection target 2 with reference to the adaptive mental state determining condition Ca. In other words, through the data collecting process and the detection condition training process in the drowsiness detection method of the embodiment, the detection/control circuit 10 of the embodiment is capable of identifying the adaptive mental state determining condition Ca suitable for the detection target 2. Thus, through the optimized adaptive mental state determining condition Ca for the detection target 2, the detection/control circuit 10 is allowed to implement the drowsiness monitoring operation with better accuracy on the detection target 2.

For example, the detection condition training process in the drowsiness detection method of the embodiment includes the following steps. In Step (a"), the detection/control circuit 10 detects the physiological symptom information Is of the detection target 2. In Step (b"), the detection/control circuit 10 determines whether the physiological symptom information Is satisfies the adaptive mental state determining condition Ca. When the physiological symptom information Is does not satisfy the adaptive mental state determining condition Ca, it means the detection target 2 is not in a drowsy mental state. Accordingly, the drowsiness detection method of the embodiment iterates Step (a") to continue in detecting the physiological symptom information Is of the detection target 2. Conversely, when the physiological symptom information Is satisfies the adaptive mental state determining condition Ca, it means the physiological symptom information Is of the detection target 2 satisfies the drowsy state defined in the adaptive mental state determining condition Ca, and it is much likely that the detection target 2 is in a drowsy state. Accordingly, the drowsiness detection method of the embodiment performs Step (c"). In Step (c"), the detection/control circuit 10 correspondingly determines that the detection target 2 is in a drowsy mental state.

In this embodiment, an example of identifying one adaptive mental state determining condition Ca in the detection condition training process in the drowsiness detection method of the embodiment is described for illustrative purposes rather than limiting the present invention thereto. In an alternative example, two or more adaptive mental state determining conditions respectively corresponding to two or more different mental states may be simultaneously identified in the detection condition training process in the drowsiness detection method of the embodiment. For example, two adaptive mental state determining conditions Ca and Cb are identified in the detection condition training process. The adaptive mental state determining conditions Ca and Cb respectively indicate the strength distribution standards of the components α, β, θ and δ of the brainwave time-domain waveforms of the detection target 2 as the detection target 2 enters a drowsy state and a light sleep state.

In a situation where two adaptive mental state determining conditions Ca and Cb are present, the drowsiness monitoring process in the drowsiness detection method of the embodiment further includes Steps (d") and (e"). More specifically, after Step (c"), when the physiological symptom information Is does not satisfy the adaptive mental state determining condition Ca, the drowsiness detection method of the embodiment performs Step (d"). In Step (d"), the detection/control circuit 10 determines whether the physiological symptom information Is satisfies the adaptive mental state determining condition Cb. When the physiological symptom information Is does not satisfy the adaptive mental state determining condition Cb, it means the detection target 2 is not in a drowsy state or a light sleep state, and the drowsiness detection method of the embodiment iterates Step (a") to continue in detecting the physiological symptom information Is of the detection target 2. Conversely, when the physiological symptom information Is satisfies the adaptive mental state determining condition Cb, it means the physiological symptom information Is of the detection target 2 satisfies the light sleep state defined in the adaptive mental state determining condition Cb, and the detection target 2 is much likely in a light sleep state. Accordingly, the drowsiness detection method of the embodiment performs Step (e"). In Step (e"), the detection/control circuit 10 correspondingly determines that the detection target 2 is in a light sleep mental state.

In this embodiment, an example of identifying two adaptive mental state determining conditions in the detection condition training process in the drowsiness detection method of the embodiment is described for illustrative purposes rather than limiting the present invention thereto. In an alternative example, three or more adaptive mental state determining conditions may be identified to provide a more versatile drowsiness monitoring operation for the detection target 2. For example, four adaptive mental state determining conditions can be identified in the detection condition training process by the detection/control circuit 10. The four adaptive mental state determining conditions may respectively correspond to a drowsy state, a light sleep state, a deep sleep state and an eyeball movement period state.

It should be noted that, in this embodiment, the detection/control circuit 10 is a single module for example. In another embodiment, the detection/control circuit 10 may be implemented by two modules, e.g., a detection module and a core processing circuit. More specifically, the detection module implements the operation for detecting the physiological symptom information of the detection target 2; the core processing circuit controls the modules in the drowsiness detection device 1 and performs miscellaneous operations, and may be implemented by a processor and a random access memory (RAM).

In conclusion, the drowsiness detection method of the embodiment includes the data collecting process, in which the detection/control circuit is utilized to detect the physiological symptom information of the detection target. When the physiological symptom information satisfies the predetermined drowsiness threshold condition, the stimulation triggering circuit and the response circuit are utilized to test stimulations and response detections of the detection target to truly record the physiological symptom information of the detection target at the time point as the detection target enters a drowsy state. In other words, the drowsiness detection method of the embodiment, through actual tests on triggering the stimulation event and determining the response event from the detection target, identifies the physiological symptom information of the detection target as the detection target enters a drowsy state. Therefore, compared to a conventional drowsiness detection device, the drowsiness detection method and associated device according to the embodiment of the present invention more flexibly provides drowsiness detection operations with higher accuracy for different types of users under detection.

While the invention has been described by way of example and in terms of the preferred embodiments, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A drowsiness detection method, for performing a drowsiness detection operation on a detection target, the drowsiness detection method comprising a data collecting process, the data collecting process comprising:
    a) detecting, by a detection/control circuit, first brainwave symptom information of the detection target;
    b) determining, by the detection/control circuit, whether the detection target satisfies a predetermined drowsiness threshold condition according to the first brainwave symptom information, and performing Step (c) if a result is affirmative;
    c) triggering, by a simulation triggering circuit connected to the detection/control circuit, a stimulation event on the detection target in response to a driving signal provided by the detection/control circuit when the detection target satisfies the predetermined drowsiness threshold condition;
    d) within a predetermined period after step (c), determining, by a response circuit connected to the detection/control circuit, whether a response event, triggered by the detection target in response to the stimulation event, is detected, wherein in response to the response event the response circuit provides a response signal to the detection/control circuit and the response event is a man-machine-interface response event;
    e) determining, by the detection/control circuit, whether the stimulation event satisfies a threshold strength condition when the response event is not detected;
    f) recording, by the detection/control circuit, the first brainwave symptom information as a drowsiness detection condition corresponding to the detection target when the stimulation event satisfies the threshold strength condition; and
    g) increasing, by the detection/control circuit, a strength of the stimulation event when the stimulation event does not satisfy the threshold strength condition, and iterating step (c);
    wherein the data collecting process further comprises adjusting the threshold strength condition and iterating steps (a) to (g) to obtain a plurality of the drowsiness detection conditions corresponding to different threshold strength conditions of the detection target.

2. The drowsiness detection method according to claim 1, further comprising a detection condition training process performed by the detection/control circuit, the detection condition training process comprising:
    a') establishing an artificial neural network; and
    b') entering the drowsiness detection conditions of the detection target into the artificial neural network to identify and store a first adaptive mental state determining condition corresponding to the detection target.

3. The drowsiness detection method according to claim 2, further comprising a drowsiness monitoring process performed by the detection/control circuit, the drowsiness monitoring process comprising:
    a") detecting second brainwave symptom information of the detection target;
    b") determining whether the second brainwave symptom information satisfies the first adaptive mental state determining condition; and
    c") determining the detection target as in a first mental state when the second brainwave symptom information satisfies the first adaptive mental state determining condition.

4. The drowsiness detection method according to claim 3, wherein the drowsiness monitoring process further comprises:
    d") iterating step (a") when the second brainwave symptom information does not satisfy the first adaptive mental state determining condition.

5. The drowsiness detection method according to claim 3, wherein the detection condition training process further comprising the detection/control circuit identifies and stores a second adaptive mental state determining condition corresponding to the detection target based on the drowsiness detection conditions corresponding to the detection target entered into the artificial neural network.

6. The drowsiness detection method according to claim 5, wherein the drowsiness monitoring process further comprises:
    d") determining whether the second brainwave symptom information satisfies the second adaptive mental state determining condition when the second brainwave symptom information does not satisfy the first adaptive mental state determining condition; and
    e") determining the detection object as in a second mental state when the second brainwave symptom information satisfies the second adaptive mental state determining condition.

7. A drowsiness detection device, for performing a drowsiness detection operation on a detection target, comprising:
    a detection/control circuit, for detecting first brainwave symptom information of the detection target, determining whether the detection target satisfies a predetermined drowsiness threshold condition according to the first brainwave symptom information, and further providing a driving signal when the detection target satisfies the predetermined drowsiness threshold condition;

a stimulation triggering circuit, for triggering a stimulation event on the detection target in response to the driving signal; and a response circuit, for detecting a response event triggered by the detection target in response to the stimulation event, and accordingly providing a response signal to the detection/control circuit, wherein the response event is a man-machine-interface response event;

wherein, the detection/control circuit further detects whether the detection target correspondingly triggers the response event according to the response signal within a predetermined period from the simulation event, determines whether the stimulation event satisfies a threshold strength condition when the response event is not detected, and records the first brainwave symptom information as a drowsiness detection condition corresponding to the detection target when the stimulation event satisfies the threshold strength condition;

wherein the detection/control circuit further increases a strength of the stimulation event when the stimulation event does not satisfy the threshold strength condition, and triggers the stimulation event with the increased strength on the detection target to detect the response event corresponding to the stimulation event with the increased strength on the detection target; and wherein the detection/control circuit further adjusts the threshold strength condition and drives the drowsiness detection device to obtain a plurality of the drowsiness detection conditions corresponding to different threshold strength conditions.

8. The drowsiness detection device according to claim 7, wherein the detection/control circuit further establishes an artificial neural network, and enters the drowsiness detection conditions of the detection target into the artificial neural network to identify and store a first adaptive mental state determining condition corresponding to the detection target.

9. The drowsiness detection device according to claim 8, wherein the detection/control circuit further detects a second brainwave symptom information of the detection target, determines whether the second brainwave symptom information satisfies the first adaptive mental state determining condition, and determines the detection target as in a first mental state when the second brainwave symptom information satisfies the first adaptive mental state determining condition.

10. The drowsiness detection device according to claim 9, wherein the detection/control circuit again detects the second brainwave symptom information when the second brainwave symptom information does not satisfy the first adaptive mental state determining condition.

11. The drowsiness detection device according to claim 9, wherein the detection/control circuit further identifies and stores a second adaptive mental state determining condition corresponding to the detection target based on the drowsiness detection conditions of the detection target entered into the artificial neural network.

12. The drowsiness detection device according to claim 11, wherein the detection/control circuit determines whether the second brainwave symptom information satisfies the second adaptive mental state determining condition when the second brainwave symptom information does not satisfy the first adaptive mental state determining condition, and determines the detection object as in a second mental state when the second brainwave symptom information satisfies the second adaptive mental state determining condition.

\* \* \* \* \*